United States Patent [19]

Kristinsson et al.

[11] Patent Number: 5,718,925
[45] Date of Patent: Feb. 17, 1998

[54] APPARATUS FOR MAKING A PROSTHESIS SOCKET

[75] Inventors: Össur Kristinsson, Reykjavik; Tryggvi Sveinbjörnsson, Gardabær; Hilmar Br. Janusson, Seltjarnarnes; Gudni Ingimarsson, Reykjavik, all of Iceland

[73] Assignee: Ossur hf., Reykjavik, Iceland

[21] Appl. No.: 559,311

[22] Filed: Nov. 15, 1995

[51] Int. Cl.$^6$ .................................................. A61F 2/60
[52] U.S. Cl. .................. 425/2; 264/573; 264/DIG. 30; 623/33; 623/901; 425/389
[58] Field of Search ................ 425/2, 389; 264/222, 264/223, DIG. 30, 573; 623/33, 901

[56] References Cited

U.S. PATENT DOCUMENTS

| | | | |
|---|---|---|---|
| 980,457 | 1/1911 | Toles | 623/37 |
| 2,424,278 | 7/1947 | Kunkel | 264/222 |
| 3,601,819 | 8/1971 | Herrmann | 623/33 |
| 4,411,262 | 10/1983 | von Bonin et al. | 128/90 |
| 4,502,479 | 3/1985 | Garwood et al. | 128/90 |
| 4,635,626 | 1/1987 | Lerman | 128/165 |
| 4,667,661 | 5/1987 | Scholz et al. | 128/90 |
| 5,133,777 | 7/1992 | Arbogast et al. | 264/DIG. 30 |
| 5,163,965 | 11/1992 | Rasmusson et al. | 623/36 |
| 5,226,918 | 7/1993 | Silagy et al. | 623/33 |
| 5,228,164 | 7/1993 | Graf et al. | 12/133 R |
| 5,258,036 | 11/1993 | Edenbaum et al. | 264/222 |
| 5,263,990 | 11/1993 | Handal | 623/57 |
| 5,354,259 | 10/1994 | Scholz et al. | 428/240 |
| 5,468,140 | 11/1995 | Hoffman et al. | 425/389 |
| 5,503,543 | 4/1996 | Laghi | 425/2 |

FOREIGN PATENT DOCUMENTS

| | | | |
|---|---|---|---|
| 1018633 | 5/1983 | U.S.S.R. | |
| 1109150 | 8/1984 | U.S.S.R. | 623/33 |
| 1195996 | 12/1985 | U.S.S.R. | 623/33 |
| 1586703 | 8/1990 | U.S.S.R. | 623/901 |
| 2149309 | 6/1985 | United Kingdom | 623/901 |

OTHER PUBLICATIONS

H. Gardner. "A Pneumatic System For Below–Knee Stump Casting". *Prosthetic International*, v. 13, pp. 12–14 (1968).
Össur, hf. brochure for ICECAST Pressurized Casting Instrument, 9 pgs., (Aug. 1993).
Wu et al. "Scotchcast® P.V.C. Interim Prosthesis for Below–knee Amputees." *Bulletin of Prosthetic Research* BPR 10–36, Fall 1981, pp. 40–45.
Össur, h.f. undated brochure for Iceross Icelandic Roll on Silicone Socket (2 pgs.).

*Primary Examiner*—Robert Davis
*Attorney, Agent, or Firm*—Bacon & Thomas

[57] ABSTRACT

A definitive socket for residual limb prosthetic use is formed in a single molding step by compressive pressure casting or molding a pre-formed, moldable, hardenable socket material over a residual limb and curing the socket material to a load-bearing hardened condition while it is maintained under peripheral compressive pressure against the residual limb and while the residual limb is tensioned in a distal direction during the casting process. The combination of pressure casting the socket material and applying tension to the residual limb in a distal direction while the socket material is curing results in forming a definitive socket that fits well to the residual limb after curing without substantial rectification. Pressure relief formations, socket coverings, and a prosthesis coupler may be compression molded simultaneously with the socket. A pressure casting system for carrying out the casting of the socket includes a pressure chamber, a compressive pressure applying membrane, a tension reacting system for producing a resultant axial tension in the residual limb within the socket material during forming and hardening of the socket and optionally a load cell to monitor or indicate the tension force applied during molding. The socket material includes a pre-formed tubular sleeve-like reinforcement web of fibers pre-impregnated with an uncured preferably water activatable, moldable, hardenable resin material, with an integrated prosthesis coupler at one end.

3 Claims, 7 Drawing Sheets

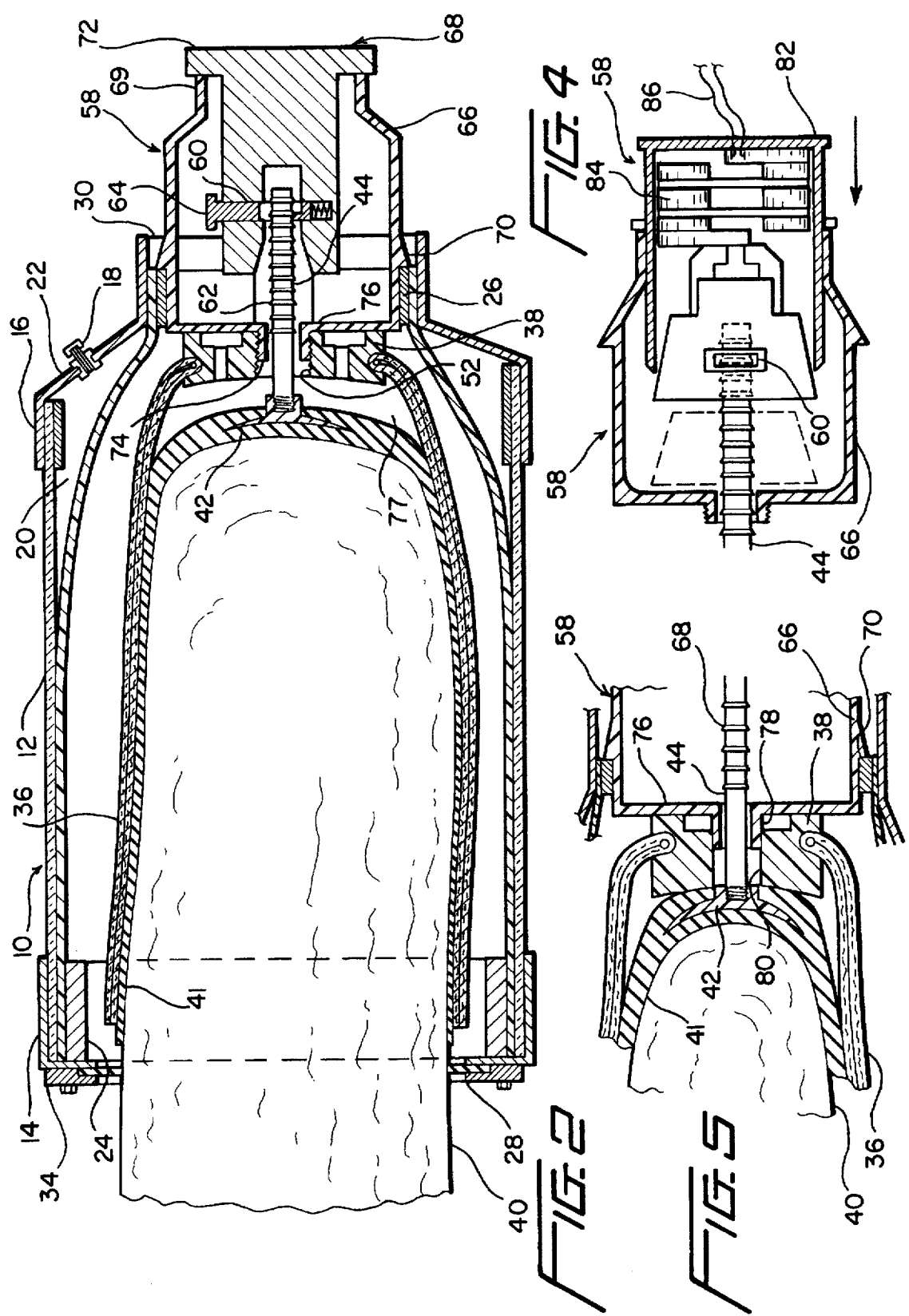

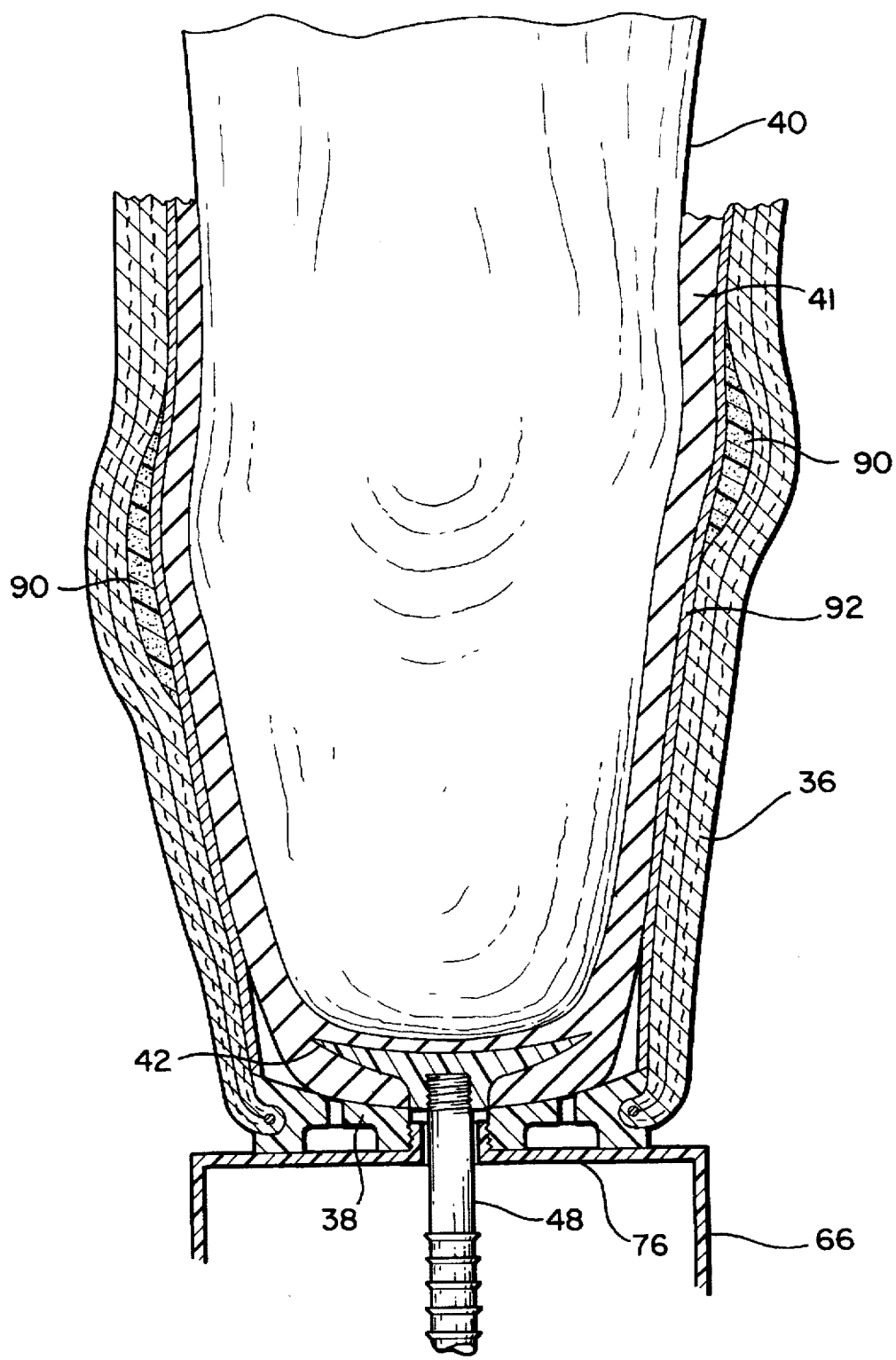

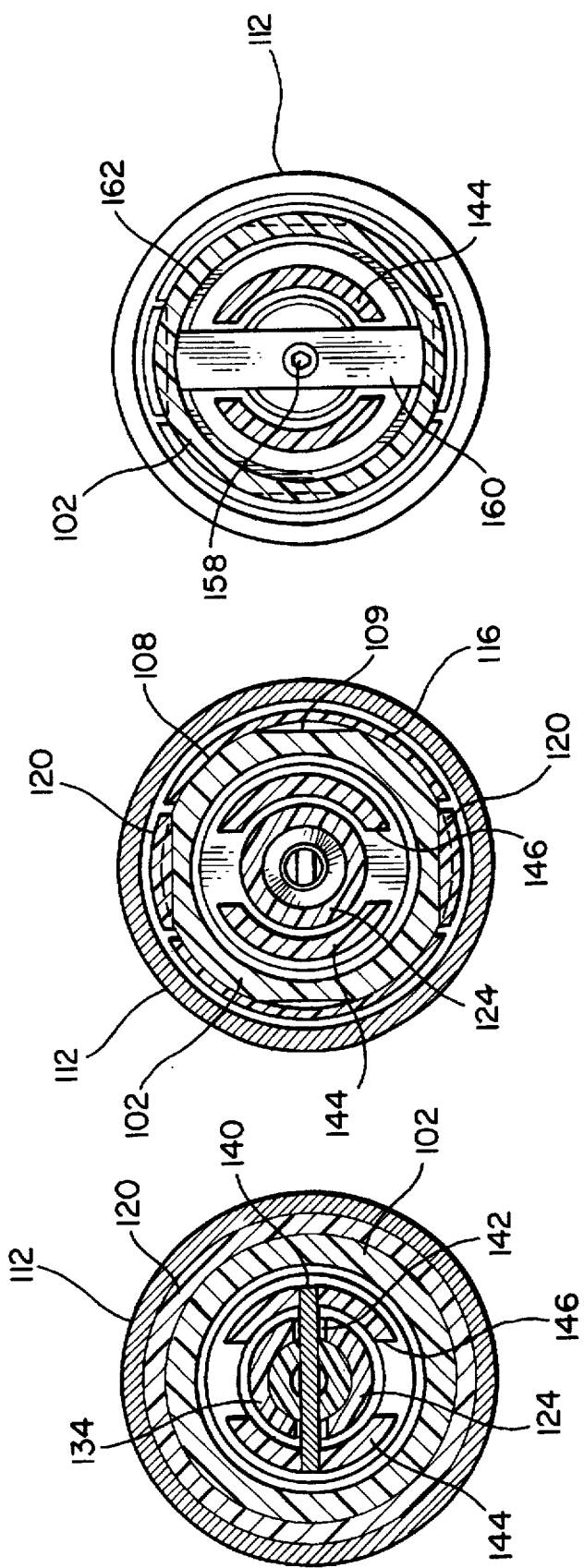

APPARATUS FOR MAKING A PROSTHESIS SOCKET

FIELD OF THE INVENTION

This invention relates to a method and apparatus for making a definitive prosthesis socket for fitting residual limbs to prostheses and a resultant prosthesis socket.

BACKGROUND OF THE PRIOR ART

Definitive sockets for fitting prostheses to residual limbs of amputees are made by various processes in accordance with prior art techniques, including molding thermosetting, thermoforming or other known resinous materials to obtain a final rigid socket shape that will receive a residual limb and structurally react loads between the prosthesis and the residual limb without discomfort to the user. Such molded sockets without and with reinforcements are exemplified in U.S. Pat. Nos. 5,163,965, granted Nov. 17, 1992 to Rasmusson and Fischl; and 5,263,990, granted Nov. 23, 1993 to Handal, respectively.

In accordance with a well known technique for molding definitive sockets of resinous materials, a male or positive mold of the residual limb area is made from a plaster of paris female or negative casting sleeve that has been formed by molding the sleeve directly against the residual limb, sometimes with the aid of a known pressure casting system of the type exemplified by the ICECAST™ system made by Össur h. f. of Reykjavik, Iceland. The positive mold is then adjusted or "rectified" in accordance with well known techniques to provide relief for sensitive areas of the residual limb and to obtain a correctly sized socket that will properly fit the residual limb. The multiple step molding and rectification process is well known and has been extensively described in literature and texts known to prosthetists. The process is time-consuming, expensive and heavily dependent on the individual skills of the prosthetist.

Other procedures for molding interim or definitive sockets have been described in the prior art, including a procedure whereby SCOTCHCAST® tape made by 3M Company of Minneapolis, Minn., has been utilized to produce an interim prosthesis socket for below-knee amputees. The SCOTCHCAST® tape was wrapped directly over the residual limb after a tube sock was applied to the residual limb and manual compressive pressure was applied to the SCOTCHCAST® tape while it was curing to a hardened condition to provide relief for the patellar tendon area to form a PTB bar and to control the anterior-posterior diameter for weight bearing. (Wu et al., "SCOTCHCAST® P.V.C. Interim Prosthesis for Below-Knee Amputees", *Bulletin of Prosthetics Research* 10-36, Fall 1981, pp. 40–45). This process, however, has not been reported as being suitable for forming definitive prosthesis sockets suitable for continuous long-term use.

BRIEF SUMMARY OF THE INVENTION

The present invention is concerned with a molded residual limb definitive prosthesis socket formed by using a single step pressure casting technique that enables the production of the socket with an internal form that is substantially in finished condition upon completion of the casting process. The socket is molded directly on a residual limb using a reinforced resinous material that in a preferred form of the invention is pre-formed as a pre-impregnated ("pre-preg") tubular mat or web of reinforcing strands or elements impregnated with a hardenable uncured or unhardened moldable preferably resinous material that is assembled with a suitable prosthesis coupler that is ultimately unified with the molding material during molding and curing of the socket. Suitable liner and covering fabric layers may be bonded to the inner and outer surfaces of the socket material during molding and pressure relieving resilient material may be incorporated in the socket during molding as well.

The molding of the socket is carried out using a compressive pressure casting technique modified so that tension is applied to the distal end of the residual limb in the distal direction during hardening of the socket material. In a preferred embodiment of the invention, the tension is applied through a resilient, impermeable suction socket or sleeve that has been placed on the residual limb between the limb and the socket material. It has been discovered that the application of such tension to the residual limb distally distends the soft tissue of the residual limb relative to the underlying skeletal bone(s) and reduces it in size diametrically. The application of such tension during pressure casting of the socket material produces a virtually final or definitive desired fit between the residual limb and the socket. Thus, this invention reflects the discovery that the combination of tension applied to the distal end area of the residual limb and compression casting of the socket material directly on the residual limb while under such tension enables a prosthetist to mold a definitive socket for prosthetic use in a single step using a moldable and hardenable socket material that possesses the necessary load bearing structural characteristics for a prosthesis socket.

A preferred moldable curable socket material in accordance with this invention comprises a tubular mat of braided carbon fiber reinforcing strands impregnated with a water curable polyisocyanate type prepolymer. The exemplary socket pre-form assembly includes a prosthesis coupler element integrated into one end of the socket assembly before molding and hardening.

DESCRIPTION OF THE DRAWINGS

FIG. 2 shows a side elevation section view of a pressurized casting device constructed in accordance with the invention with a residual limb, residual limb suction sleeve and socket pre-form in position for casting a residual limb socket intended to cooperate with a prosthesis;

FIG. 3 is a side elevation section view showing a detail of the residual limb suction sleeve, prosthesis coupler and socket pre-form with pressure relief inserts in place;

FIG. 4 shows a partial section elevation view of the tension connector element of the pressurized casting device in accordance with this invention incorporating a tension measuring arrangement;

FIG. 5 is a partial section elevation view illustrating an alternate arrangement of the residual limb socket sleeve and socket pre-form in position for casting;

FIG. 10 is a section view taken along line 10—10 of FIG. 9;

FIG. 11 is a section view taken along line 11—11 of FIG. 9; and

FIG. 12 is a section view taken along line 12—12 of FIG. 9.

DETAILED DESCRIPTION OF PREFERRED EMBODIMENTS OF THE INVENTION

In accordance with prior art techniques for making residual limb sockets intended to receive a prosthesis for the limb, a female mold is typically formed by a casting technique whereby a water activatable moldable and hardenable or curable wrapping (e.g., plaster of paris bandage) is applied in soft pre-hardened condition over the distal residual limb area, the wrapping is permitted to set up or harden while it is pressurized by a pneumatically driven bladder or membrane against the residual limb area, and after hardening (curing), the wrapping is removed from the residual limb area so as to provide a female cavity duplicating the residual limb distal end contour.

A positive cast of the residual limb distal end area is then made using the female cavity as a female mold and finally after suitable adjustments or rectifications of the mold are made, a definitive socket is molded by casting or forming a suitable hardenable socket structural material over the positive cast. Various finishing operations are then performed on the socket to make it ready for use and to receive the prosthesis.

In a typical prosthesis socket assembly, the definitive socket will incorporate suitable hardware including adjustable prosthesis connector elements so as to enable a rigid yet releasable connection to be made between the definitive socket and the prosthesis. One part of such hardware is referred to herein as the prosthesis coupler for convenience and is intended to designate the end fitting for the socket that ultimately forms the distal load reacting connection between socket and prosthesis.

Figure 1:
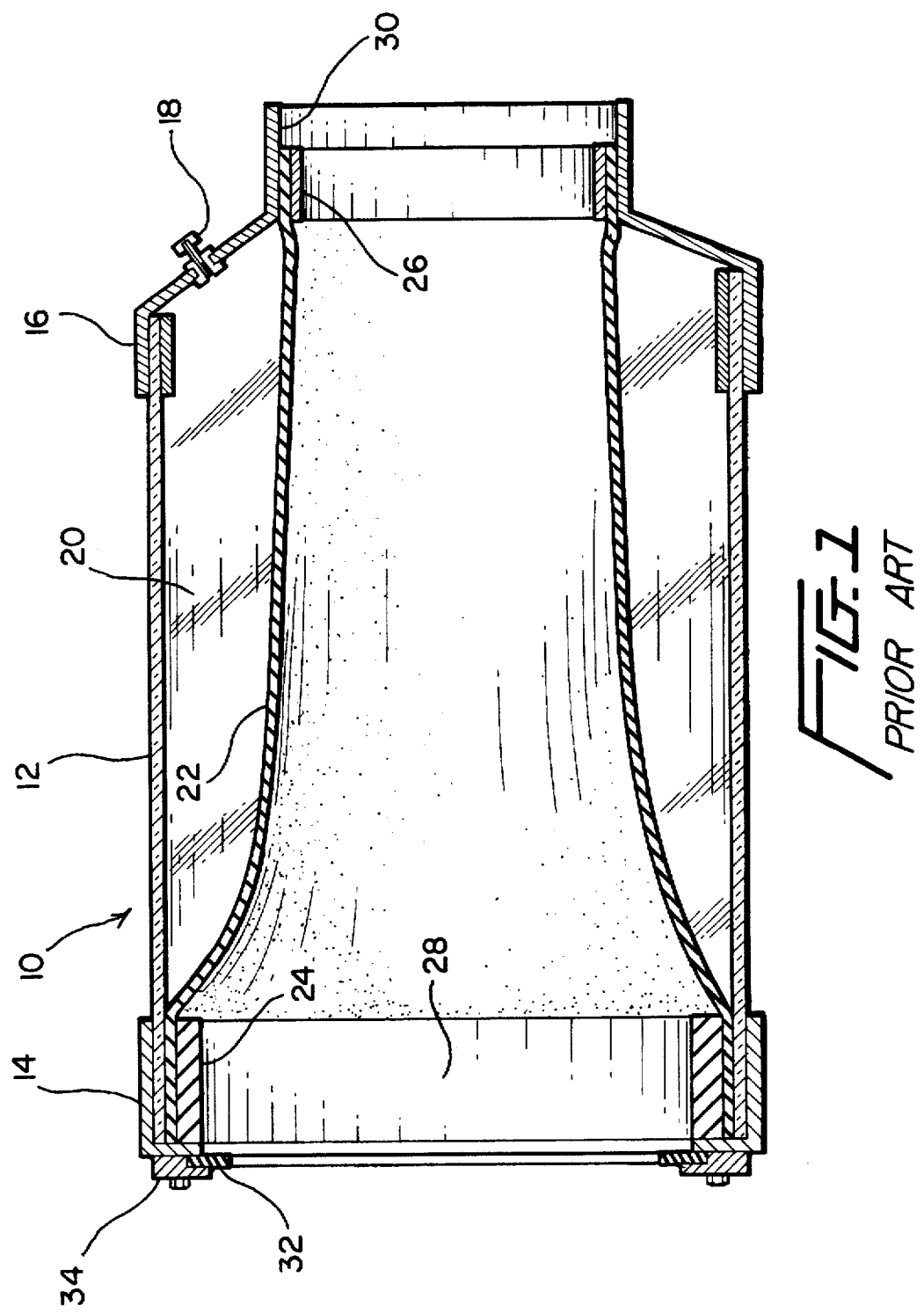
FIG. 1 illustrates a side elevation section view of a pressurized casting device constructed in accordance with the prior art.

With reference to FIG. 1, a prior art example of a pressurized casting device 10 is shown that has been successfully used to support and pressurize female mold casting sleeves applied to residual limb areas during hardening or curing of the mold sleeves to ensure that the mold sleeves will conform precisely to the external configuration of the residual limb areas. The soft tissue of the limb is gently compressed under pneumatic pressure uniformly applied over substantially the entire external periphery of the residual limb area (pressure is avoided at the limb distal tip area) through such a casting system.

The casting device 10 includes a rigid outer housing that includes a transparent tubular member 12, a proximal end cap 14 and a distal end cap 16. The distal end cap 16 includes a pressurizing fluid admitting and venting nipple 18 through which pressurizing medium (e.g., compressed air) may be admitted into the pressurizing space 20 between the housing tube 12 and pressure membrane or bladder 22 installed within the housing. The nipple 18 also permits withdrawal of air by suction from the pressurizing space 20 to expand the pressure membrane 22 outwardly towards the tubular member 12, for purposes to be explained below.

In this example, pressure membrane 22 comprises a compliant, elastomeric silicone rubber tubular member clamped in fluid-tight relationship between the clamping rings 24, 26 and the end caps 14, 16, respectively, so as to define the pressuring space 20 between the exterior of the membrane 22 and the interior of the tubular member 12 (and the interior of the end caps 14, 16, of course).

The end cap 14 is configured to provide an annular residual limb receiving opening 28 at the proximal end of the tubular member 12, while end cap 16 is shaped to provide an opening 30 having a reduced cross-sectional area as compared with opening 28 at the distal end of the tubular member 12.

The tubular membrane 22 is installed in the tubular member 12 by stretching the smaller silicone rubber tubular membrane radially outwardly at the proximal end of the tube and clamping it in place with ring 24, while the membrane is clamped in end cap 15 by an internal clamp ring 26 expanded within end cap 15 to about the normal relaxed diameter of the membrane or slightly larger. The pressure membrane 22 is maintained in longitudinal or axial tension along its length so that in its assembled condition it appears approximately as illustrated in FIG. 1, without wrinkled or collapsed portions.

An annual fitting ring 32 is removably clamped by a fastener 34 to the proximal end of the end cap 14 to close the space between a residual limb inserted into the casting device and the proximal end of the end fitting 14 to prevent blowing out of the membrane 22 through the proximal end of the tubular member 12 during a casting procedure when the membrane is pressurized. Various sizes of fitting rings 32 are made available for use with the casting device to accommodate various sizes of residual limbs over which the casting device is to be placed.

In operation, to create a casting sleeve using the exemplary casting device shown in FIG. 1, a residual limb area is first prepared by donning a silicone rubber sleeve of the type sold under the name, ICEROSS™, manufactured by Össur h. f. of Reykjavik, Iceland, over the residual limb area. This type of silicone sleeve gently stretches the soft tissue of the residual limb area in the distal direction beneath the sleeve when it is donned by rolling the sleeve over the limb distal end area and effectively stabilizes the soft tissue. However, the stretching essentially only occurs at the surface of the limb and is not to be considered the same or equivalent to a tension applied from externally of the silicone sleeve to the limb distal end area. The silicone sleeve is also referred to as a suction socket because of how it interacts with the residual limb, which will be explained below.

A water settable moldable casting sleeve material, such as plaster of paris impregnated tape or bandage, is soaked in water and then wrapped over the suction socket while being formed by hand to smoothly conform to the limb distal end area shape. A fabric stocking may then be placed over the still soft casting sleeve material and then the pressure casting device 10 if fit over the residual limb area and casting material so that the residual limb enters the device 10 through the proximal opening 28 (sometimes referred to herein as the residual limb receiving end of the casting device). A suction is usually applied to the pressurizing space 20 through nipple 18 before the residual limb is inserted in the casting device 10 so as to draw the pressurizing membrane away from the central area of the casting device to provide space for the residual limb and the casting material within the central area.

A spacer cup device (not shown) may be fitted within the pressure membrane between the residual limb distal end and the distal end of the pressure casting device housing to limit or avoid pressurization of the distal tip end of the residual limb through the pressure membrane. A suitable spacer device may also be used to ensure that a space is maintained between the distal end of the limb with the casting material thereon and the cup device to permit expansion of the distal end of the soft tissue of the limb longitudinally towards the cup device during the pressurized casting procedure.

The pressurizing space 20 is now pressurized via the nipple 18 by using compressed air from a suitable regulated source to thereby force the pressure membrane into compressive contact with the casting material and to uniformly pressurize the casting material about the residual limb. The soft tissue of the residual limb reacts to the pressure as it was subjected to a hydrostatic force exerted uniformly over the entire surface of the residual limb, but not against the distal end of the limb due to the presence of the spacer cup.

In actuality, the pressure acting in the pressurized casting device tends to urge the casting device and its associated elements longitudinally away from the distal end of the residual limb and to urge the residual limb back out of the opening 28. However, the compression and tension forces are stabilized within the membrane 22 while the casting material is permitted to set up and harden in place within the pressurized casting device while pressure is applied to the casting material and the contained residual limb. External tensioning is not applied to the residual limb area during this known procedure.

After sufficient time has elapsed to permit curing of the casting sleeve material, the pressurized space 20 is vented to release the casting sleeve material from pressurization and the casting device 10 is removed from the residual limb. Again, a vacuum may be applied to the space 20 to draw the membrane 22 away from the external surface of the cast sleeve to permit easy withdrawal of the residual limb from the central area of the casting device.

The hardened casting sleeve material, now in the form of a female molding sleeve, is removed from the residual limb area in accordance with known techniques using a cutting tool to split the sleeve, if necessary. The sleeve is then subjected to further processing, and ultimately is used to make a male or positive mold of the residual limb area using the cast molding sleeve as a female mold. The positive mold is further processed or rectified to adjust the mold surface to a final size and configuration, and to take into account pressure points that are known or expected to exist between the residual limb and definitive socket. Typically, pressure reliefs are needed in the final definitive socket to take into account the shape and configuration of the residual limb distal area, the presence of bone tissue near the surface of the limb, and other variables or factors that are well known to prosthetists. The final or definitive prosthesis socket is thus formed using the male mold in accordance with known techniques.

The present invention contemplates apparatus and methodology for forming a definitive prosthesis socket in essentially a single step casting operation that eliminates the need for making female casting sleeves and positive molds as well as much of the associated rectification and fitting work involved in the prior art procedure.

More specifically, with reference to FIG. 2, the known pressure casting device 10 is utilized in conjunction with a socket pre-form 36 made in accordance with this invention, the pre-form including an integrated prosthesis coupler 38 to form a definitive prosthesis socket in a single casting step using both compression and tension simultaneously applied to the residual limb distal area during a molding procedure.

As shown in FIG. 2 in the preferred embodiment of the invention, the distal end of a residual limb 40 is covered first by a silicone suction sleeve 41 such as the ICEROSS™ described above. The silicone sleeve includes an integrated end fitting 42 into which a tension pin or rod (or tension transfer element) 44 may be screwed or otherwise secured (see FIG. 3) to provide a means for transmitting axial tension or compression force through the distal end wall of the silicone sleeve 41.

Tension pins such as pin 44 have been used with such silicone suction sleeves for securing the sleeves in a prosthesis socket but have not been used in the manner set forth herein for tensioning a residual limb 40 during pressure casting of a definitive prosthesis socket.

Figure 6:
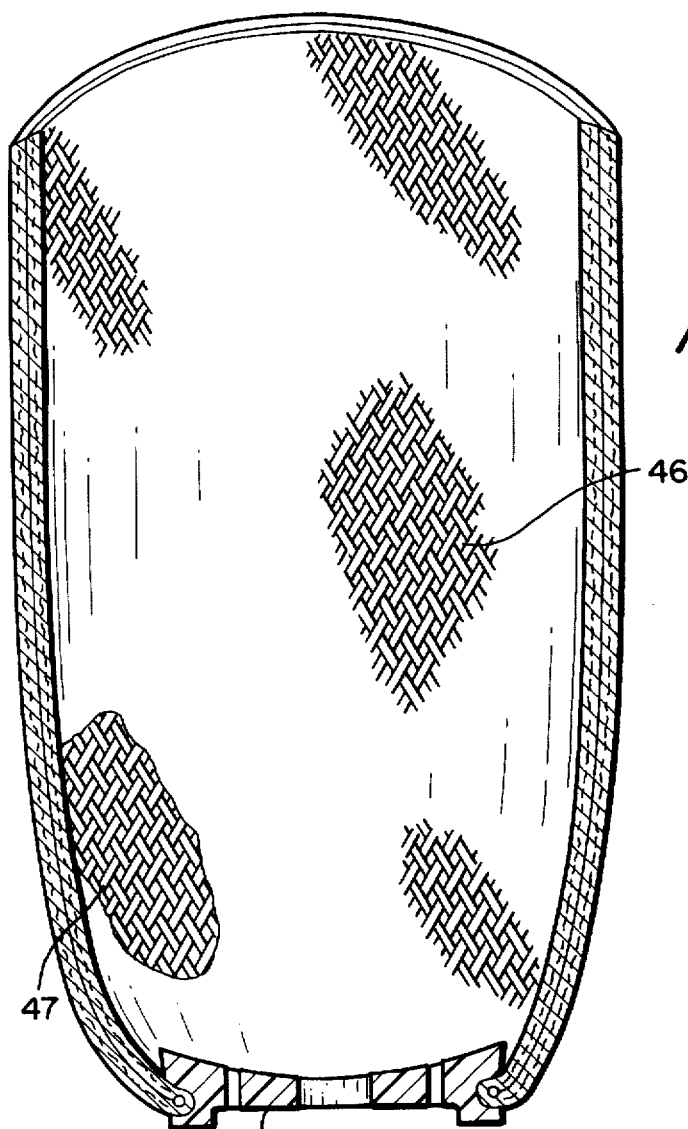
FIG. 6 is a partial section view of a preferred embodiment of the reinforcement used to form the socket pre-form.

The socket pre-form 36 in accordance with a preferred form of this invention comprises any suitable combination of hardenable moldable compounds and reinforcement materials that will achieve the formation of a definitive socket having physical characteristics necessary or desirable for such a definitive socket, and a prosthesis coupler or the equivalent. A preferred embodiment of a socket pre-form comprises a porous or web-like compliant tubular braided carbon fiber sleeve 46 (see FIG. 6) available from Atkins & Pierce, 2 Braid Way, Covington, Ky. as product numbers WGM4, WGM5.00 and WGM6.00 (4", 5" and 6" biaxial carbon fiber sleeves), pre-impregnated with a water curable polyisocyanate type pre-polymer resin 47 available under I.D. No. 41-3701-0524-3 from 3M Company of Minneapolis, Minn. The resin is activated and rendered moldable by the addition of water to the resin and after wetting the resin cures to a hardened condition rapidly.

More specifically, the braided carbon fiber sleeve is impregnated with the resin so that the ratio by weight of resin to the weight of fiber (not counting the prosthesis coupler at the end of the sleeve) is about 50%. This ratio could be varied to suit particular applications so that resin amounts as little as about 35% by weight and as much as about 75% could theoretically be used.

Resins and reinforcements potentially suitable for use in forming the pre-form 36 are described in U.S. Pat. Nos. 4,502,479 granted to Garwood et al. on Mar. 5, 1985; 4,667,661 granted to Scholz et al. on May 26, 1987 and 5,228,164 granted to Graf et al. on Jul. 20, 1993; all of which are assigned to 3M Company; and U.S. Pat. No. 4,411,262 granted to Bonin et al on Oct. 25, 1983, assigned to Bayer (Germany); and all of which are herein incorporated by reference for their descriptions of various formulations of water activatable polyisocyanate resins and reinforcing materials potentially usable for making preforms that may be used in the casting device and methodology described and claimed herein.

Of course, resin-reinforcement combinations would be selected on the basis of their storage (shelf life), molding and hardening characteristics such that the final socket would be structurally rigid and capable of bearing loads imposed on such sockets during actual use.

The pre-form 36 normally is packaged in rolled-up condition in a hermetically sealed pouch and is activated by soaking the pre-form in water to render the pre-form soft and compliant. The wet pre-form can be manually donned over the residual limb and silicone sleeve by manipulation and also can be manually smoothed and initially pressed against the limb area in preparation for inserting the limb, silicone sleeve, pre-form and their associated elements into the molding device, all in accordance with the description presented hereinabove and below.

Use of reinforcement materials and other elements constituting the final definitive socket or the pre-form 36 that detract from moldability, shelf life or strength are to be avoided for obvious reasons.

The presently preferred resin identified as 3M No. 41-3701-0524-3 is composed as follows:

| MATERIALS | % BY WEIGHT |
|---|---|
| 1,1'-methylenebis (isocyanatobenzene) | 59.00 |
| PPG 725 (glycol from Union Carbide) | 25.03 |
| PPG 425 (glycol from Union Carbide) | 9.92 |
| Pluronic F-108 (from BASF Wyandotte) | 4.00 |
| 4-2-1-methyl-2-(4-morpholinyl) ethoxy ethyl morpholine (catalyst) | 1.34 |
| 2,6-DI-tert-butyl-p-cresol | .48 |
| benzoyl chloride (stabilizer) | .05 |

The resin is in liquid form when impregnated into the reinforcement and the pre-form is in relatively firm but pliable condition within the sealed storage pouch before activation by exposure to moisture.

Figure 7:
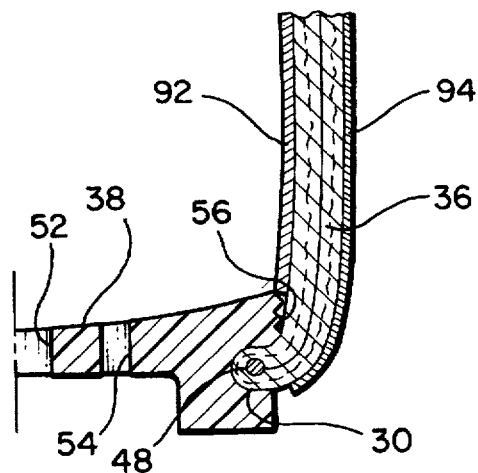
FIG. 7 is a detail section View showing the socket pre-form connected to the prosthesis coupling member and the outer layers covering the socket pre-form.

The braided sleeve may be preassembled with a prosthesis coupler 38 by folding the pre-formed sleeve over the outer surface of prosthesis coupler 38 and securing the sleeve thereto in an appropriate manner, such as by using a string 48 (see FIG. 7) to hold the sleeve in a recess 50 provided in the coupler 38. Of course, any suitable attachment method could be used between fibers 46 and coupler 38. In accordance with a preferred embodiment of the invention, the braiding of the tubular form is carried out in a known "biaxial" pattern that causes the tubular form to be very compliant and to radially contract when the tube is stretched longitudinally. This enhances the compression molding of the socket pre-form 36 during the molding and curing of the pre-form.

It is also contemplated that a socket pre-form material constituted of a curable moldable and hardenable resin or the equivalent could be used for making a socket according to this invention without using a separate reinforcement or reinforcement web, or the reinforcement could be in a different form than a pre-preg web. It is only required that the material be moldable and hardenable during compression molding to form a structurally sound socket for prosthesis application.

To prepare the preferred exemplary socket pre-form 36 for molding, the pre-form is immersed in water to activate the resin and render it moldable about the residual limb area by manual application, in a manner to be described below. It is to be understood that the socket pre-form 36 described above is exemplary only and that other resins or curable (hardenable) compounds may be used in combination with other reinforcement elements to form the socket pre-form 36. Preferably, however, it is desirable to form the socket pre-form with its associated prosthesis coupler as a pre-formed, pre-preg assembly ready for use in the pressurized casting device 10 with a minimum of manual handling of the pre-form, other than to apply an activator agent to the resin component of the pre-form to activate its hardening or curing and to don the pre-form over the residual limb so as to place the prosthetic coupler adjacent the distal tip end of the residual limb. Thereafter, the contact between the pressure membrane 22 and the pre-form 36 should be sufficient to mold the pre-form under compressive pressure in intimate contact with the residual limb 40 while the socket material hardens or cures into a final hardened condition. A suction sleeve 41 preferably is used between the residual limb tissue and the pre-form in the example shown.

Accordingly, as illustrated in the example shown in FIG. 2, a socket pre-form 36 with its associated prosthesis coupler 38 is placed over the distal end of a residual limb 40 to which a silicone suction sleeve 41 and its associated tension pin 44 has been applied. The coupler 38 includes a central aperture 52 (see FIG. 7) that may or may not be threaded, depending on the molding arrangement to be used, and may include other apertures 54 and other geometric or structural features if desired for use as part of the prosthesis coupling arrangement. The coupler 38 also may include any desired protuberances or teeth 56 or other pronounced features such as shown to enhance the bonding and securing characteristics between the coupler 38 and the pre-form 36 in the area of the coupler 38 during molding and in the final cured socket. The coupler 38 and resin of the pre-form 36 are intimately bonded together during the casting process.

An important feature of the present invention is the use of tension applied to the silicone sleeve 41 distal end area via the end fitting 42 during circumferential compression of the socket pre-form 36 while the pre-form is curing and hardening. As noted above, the silicone sleeve 41 in accordance with this example is often referred to as a "suction socket" because it grips the residual limb in an airtight, non-slip manner. When used with a prosthesis socket, such a sleeve not only provides a soft interface between the residual limb and socket, but also prevents pumping action of the residual limb area at the distal end of the residual limb, an undesirable phenomenon that occurs with some other types of known prosthesis sockets or sleeves. The silicone sleeve achieves this effect by maintaining itself in tight yet compliant contact with the residual limb area due to the gripping force exerted by the silicone against the residual limb, which prevents air from entering the sleeve interior between the sleeve and the residual limb.

To achieve application of a tension force on the distal end of suction sleeve 41 during compression molding or casting in the casting device 10, a tension connector device generally indicated at 58 is used with the pressure casting device 10. The tension connector 58 is intended to engage tension pin 44 and prevent its motion back towards the proximal opening 28 of casting sleeve 10 during compressive pressurization of the socket pre-form 36. To facilitate engagement between the pin 44 and the tension connector 58, a known one-way detent gripper 60 is used whereby protrusions 62 on pin 44 may be pushed forwardly through the gripper 60 without stoppage in a direction towards the connector 56 (i.e., away from the proximal opening 28), but reverse motion of pin 44 is braked and locked until it is desired to release the pin 44. The pin 44 is released by using a suitable gripper release knob, pin or other element 64 that may be appropriately manipulated by the prosthetist.

The gripper 60 is well known in the art per se and such elements are used in practice to secure silicone suction sleeves, such as shown at 41, to prosthesis devices to aid in inserting a residual limb into a socket to be used with a prosthesis device. However, it is believed that such grippers have not heretofore been used in association with pressure molding or casting systems of the type described herein.

The gripper 60, in the embodiment of the invention illustrated in FIG. 2, is carried by a tension connector support arrangement that includes a tubular frame 66 and a gripper supporting plug 68 axially slidable into the distal end 69 of the frame 66. The plug 68 carries the gripper 60 and its associated mechanisms including release knob 64, and the frame 66 includes openings providing manual access to the gripper release knob 64. The frame 66, for example, may be formed of longitudinally extending struts that are circumferentially spaced to provide a cage-like enclosure for the gripper mechanism so that the release knob 64 may be manipulated through the openings in the cage-like enclosure. It will be appreciated that the plug 68 with the gripper 60 can be simply inserted into the end 69 of frame 66 to cause one-way engagement between the pin 44 and the gripper 60 after the residual limb 40, silicone sleeve 41 and socket pre-form 36 have been placed as a unit into the tubular member 12, as shown in FIG. 2. In this position, the socket pre-form 36 is in its casting position, and pin 44 extends axially through aperture 52 and coupler 38 associated with the socket pre-form 36.

The frame 66 of tension connector 58 in accordance with this example of the invention also includes a force transfer element or a longitudinal movement limiter or limiters 70 that are formed as one or more radial protrusions on the frame that engage a radial face of the ring 26 or other appropriate structure of the casting device 10 to prevent axial or longitudinal motion of the frame relative to the end cap 16 during casting, at least in the direction towards the proximal end opening 28 of the proximal end cap 14.

Thus, it will be evident that once the pin 44 is engaged with the gripper 60, and residual limb 40, silicone sleeve 41 and socket pre-form 36 are located in casting position, motion of pin 44 and the distal end of silicone sleeve 41 toward the proximal end of molding device 10 is restrained by the coupling between the pin 44 and the gripper 60, and the longitudinal motion blocking engagement between the protrusions 70 and the fixed ring 26.

The proximal end of frame 66 in accordance with the embodiment shown in FIG. 2 includes a threaded proximally extending axial extension 74 (see FIG. 2). The coupler 38, in accordance with this embodiment, includes a threaded central aperture 52 that is threadedly engaged with the axial extension 74 of frame 66 of tension connector 58. In this manner, coupler 38 may be retained in close proximity to the proximal end area 76 of frame 66 of tension connector 58.

In accordance with this embodiment, a space or gap 77 may be maintained between the distal end of silicone sleeve 41 and the inner or proximal side of coupler 38 during the molding procedure. This space 77 is maintained by the engagement between pin 44 and the gripper 60 during molding in the pressure casting device 10.

When compressive pressure is applied to the socket pre-form 36 via the pressure membrane 22 following pressurization of the pressurizing space 20 by compressed air, the compressive forces and the reaction loads tend to urge the pressure casting device 10 in a distal direction relative to the residual limb 40 while the limb itself remains stationary. By observing FIG. 2, it will be noted that any movement of the casting device 10 in a distal direction is resisted by the connection between the tension connector 58 and the pin 44. That is, forces applied in a distal direction against the interior of the tubular member 12 and its associated end caps 14, 16 will be reacted against the tension connector 58 at force transfer or movement limiters 70 and such reaction will be transmitted through the plug 68 to the gripper 60 and then to pin 44. The pin 44, in turn, will transmit distally exerted forces back into the silicone sleeve end fitting 42 so that the silicone sleeve 41 effectively receives the full tension load reacted through pin 44. The tension load applied to the silicone sleeve 41 is reacted into the residual limb 40 as a distally exerted suction and stretching force that effectively stretches the residual limb area in a distal direction while reducing its overall diameter, to the extent that the soft tissue in the residual limb area can accommodate such distention and reduction in diameter.

Actual tension loads used in practicing the inventive process and using the pressure casting device according to the invention will be determined experimentally depending upon the shape, morphology and sensitivity of the residual limb and the structure/materials constituting the pre-form 36. In practice, using the preferred 3M water activatable polyisocyanate casting material disclosed above, a pressure of 220 mm mercury within the pressurizing space 20 yielding a tension force on the order of 17–30 kgs has been found satisfactory to produce a definitive socket. However, other pressures and tension loads that do not result in a discomfort level for the amputee could be used. Also, the degree of tension used will depend upon the degree of tightness of fit between the residual limb and the definitive socket that is desired. Also, in practice it has been found useful to pre-load the tension pin 44, 166 to a predetermined level on the order of 9–12 kgs before compressing the pre-form. However, in any case, the tension produced by compression of the pre-form should always exceed any pre-load set at the tension pin.

During compression of the socket pre-form 36, it is hardening against the tensioned and somewhat narrowed residual limb area of the residual limb 40. To the extent that the compressive forces exerted against the residual limb area cause its axial elongation in the distal direction, it will be seen that this motion is readily taken up by the advancement of pin 44 further into gripper 60 so that the distal tip end of the residual limb is not effectively compressed so long as space 77 is maintained. The threaded connection at the central aperture 52 of the coupler 38 and the threaded extension 74 of frame 66 causes the axial loads in the distal direction that may be exerted by the casting device 10 to be reacted into the coupler 38 so that in effect the coupler 38 moves with the tension connector 58 relative to the residual limb 40. Accordingly, since the coupler 38 effectively moves with the tension connector 58 and end cap 16 of the casting device 10, the space 77 is maintained between the distal end of the residual limb and the coupler 38 provided that the distal end of the residual limb does not expand sufficiently to take up all of the space 77.

The combination of compressive molding forces exerted on the socket pre-form 36 while it is hardening and the tension applied in a distal direction to the residual limb area via the suction socket 41 results in forming a prosthesis definitive socket having an internal geometry that requires little or no further rectification before use as a definitive load bearing socket.

Since the braided reinforcement web of the pre-form 36 is constructed to radially contract when the tubular web is elongated, tension force applied through the tension connector 58, tension pin 44, silicone sleeve 41 and coupler 38 to the socket pre-form 36 will tend to cause the pre-form 36 to initially contract radially to thereby enhance the compression force exerted by pressure membrane 22 while the socket pre-form 36 is curing and hardening within pressure casting device 10.

It has been observed that the requirement for a space 77 may not exist in all cases and the embodiment of the invention in accordance with FIG. 5 may be utilized if such a space 77 is not required.

The embodiment of the invention illustrated in FIG. 5, wherein like reference numerals are utilized for elements corresponding to the elements already described, includes a silicone suction sleeve 41, sleeve end fitting 42, and tension pin 44 having protuberances 62 thereon for engagement with a gripper (not illustrated) carried by a frame 66 of tension connector 58. In this embodiment, an axial extension 78 of proximal end wall 76 of tension connector 58 is not threaded, but is generally cylindrical so as to engage a corresponding cylindrical aperture 80 in coupler 38 through which the extension 78 extends. The extension 78 thus serves to center the coupler in the casting device. The pin 44, as in the previous embodiment, extends through both the axial extension 78 and the aperture 80 in the coupler 38. It will be observed that, as illustrated in FIG. 5, when the socket pre-form 36, silicone sleeve 41 and residual limb 40 are located in the casting position, the distal end of the silicone sleeve 41 virtually clamps the coupler 38 between the distal end of the residual limb 40 and the proximal end wall 76 of frame 66 of tension coupler 58.

In accordance with the embodiment of FIG. 5, casting or molding of the socket pre-form is carried out in the same manner as described previously in connection with FIG. 2, whereby fluid pressure is applied by pressure membrane 22 to the exterior of the socket pre-form 36 to thereby cause both radial compression and a tension to be applied to the residual limb 40, the silicone sleeve 41 and the pre-form 36 during the casting process while the pre-form 36 is hardening. The beneficial results described previously obtained by applying such compression and tension to the residual limb within the socket pre-form during curing may be obtained with the embodiment in accordance with FIG. 5 as well.

It is contemplated that, for some applications, it may be desirable to measure or monitor the tension applied or reacted by pin 44 to the distal end of silicone sleeve 41. In accordance with the embodiment of FIG. 4, a gripper 60 is carried by a gripper and load cell assembly 82 that may be axially inserted within the distal opening of tension coupler 58 to engage the pin 44 before the socket pre-form 36 and residual limb 40 are pressurized in the casting device. The assembly 82 includes a suitable force sensing device or load cell 84 that may be electrically actuated via leads 86 so as to measure and/or monitor the tension applied to the gripper 60 during compression molding of the casting sleeve 36. Of course, the load cell 84 may take any suitable form that enables measurement of the force, whether tension or compression, reacted by pin 44 against a relatively fixed element associated with the casting device. Also, the load cell 84 may be mechanically or electromechanically operated in accordance with known state of the art techniques and arranged to receive electrical signals to and transmit load signal from load cell 84 via appropriate leads (not shown). A suitable indicator adapted to receive load signals and indicate load forces (not shown) may be provided to enable an observer to detect the amount of tension exerted by pin 44 against the distal end of the silicone sleeve 41. An exemplary load cell element that may be used is the model 802 Planar Beam Sensor made by Revere Transducers Incorporated of Cerritos, Calif., which is an electrical strain gage and beam system, and which may be used in a stacked arrangement as shown to reduce errors.

It is typically desirable to provide pressure relieving soft areas or formations within a definitive socket, such pressure relief formations normally being incorporated in the socket constructed in accordance with prior art techniques during the final definitive socket molding operation. The present invention provides a technique whereby such pressure relief formations may be incorporated into the socket pre-form 36 prior to pressure casting of the socket. As illustrated in FIG. 3, soft silicone rubber or foam pressure relief formations 90 or similar materials or elements providing equivalent functions may be provided within the socket pre-form 36 by first applying a thin smooth fabric inner liner layer 92 (for example; a finely woven or knit nylon) to the outer surface of the silicone sleeve 41 followed by application of the pressure relief formations 90 to the outer surface of the liner layer 92. The skilled prosthetist will understand how and where the pressure relief formations must be provided in accordance with known techniques whereby, when the socket pre-form 36 is hardened, the formations 90 will be bonded into place against the inner surface of the socket 36 by the resin and will be in proper position to provide pressure relief for sensitive areas of the residual limb 40 during use.

After the pressure relief formations 90 are applied to the liner layer 92, the socket pre-form 36 and coupler 38 may be applied over the liner 92 to prepare the assembly for compression casting. The assembly is then placed within the pressure casting device 10 and the casting procedure as outlined above is carried out in a manner to exert tension against the distal end of the silicone sleeve 41 while the socket pre-form 36 is curing or hardening under compression.

A smooth fabric outer covering layer 94, for example, a finely woven or knit nylon, (see FIG. 7), will normally be applied to the exterior of the socket pre-form 36 before compression and molding to provide a finished appearance on the cured socket.

Figure 8:
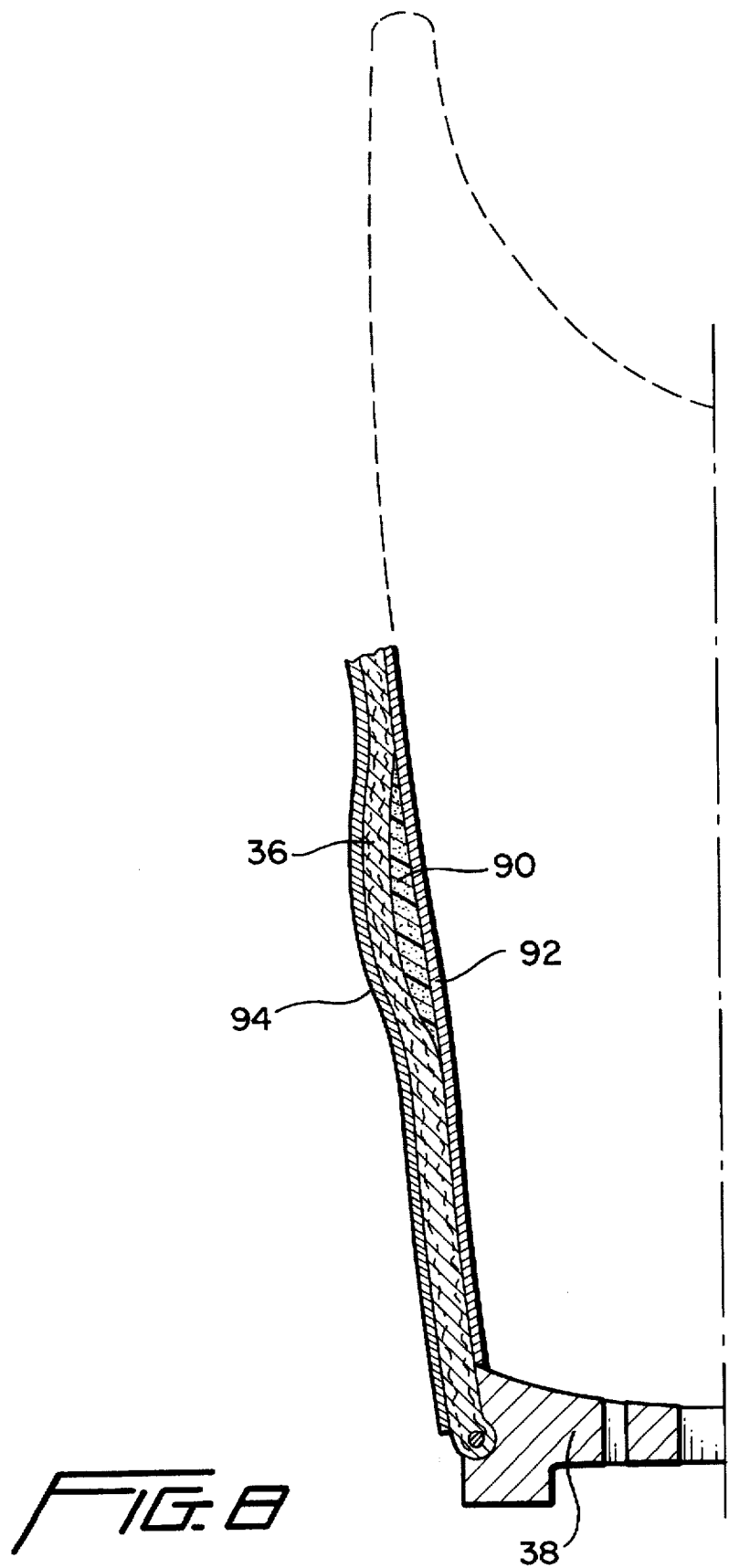
FIG. 8 is a section detail view showing the prosthesis socket and prosthesis coupler after casting and curing of the socket pre-form in accordance with this invention.

A section of a finished definitive socket substantially ready for use after removal from the casting device 10 is illustrated in FIG. 8. The material in socket pre-form 36 has hardened and, if resinous, reached a partially or fully cured state that provides a rigid definitive socket having an interior cavity that will precisely accommodate and fit the exterior contours of the residual limb with which it will be used. Further curing steps can be carried out if necessary at this stage, provided that such does not adversely affect the fit of the socket.

A prosthesis connector or joint structure will be attached to the coupler 38 and the final outer contour of the socket finished so as to provide such typical support and relief areas as are normally provided on such definitive sockets, particularly at the proximal end thereof.

With reference to FIGS. 9–12, an alternate embodiment of a preferred tension connector is illustrated. This arrangement permits accommodation of shorter residual limb lengths within the casting device and facilitates engagement and disengagement of a tension pin by a gripper mechanism.

As shown in FIGS. 9–12, a tension connector 100 comprises an elongate cylindrical member (or housing) 102 having a generally smooth inner bore 103, a proximal end 104 and a distal end 106. As shown in FIGS. 10 and 11, the outer circumference of the tubular member 102 as shown in FIGS. 10 and 11 has a smooth cylindrical periphery except for locking grooves or detents 109 that have been molded, or cut otherwise formed into the periphery of the tubular member 102 in longitudinally and circumferentially spaced relationship. The bottom of each detent groove 109 is flat, as shown in FIG. 11. The outer circumference of the tubular member 102 between the circumferentially spaced sets of detent grooves 109 as shown at 108 is smooth and uninterrupted longitudinally.

The distal end cap 110 of the casting device (that is otherwise constructed in accordance with FIG. 2) is provided with a longitudinally extending cylindrical section 112 having internal threads 114 arranged to receive a tension connector locking device 116 which, as illustrated, includes external threads cooperating with the internal threads 114 of the tubular extension 112. Pressure membrane 118 is held assembled to the end cap 110 when the tension connector locking device 116 is securely threaded into the end cap as shown. Other arrangements can be utilized for securing the tension connector locking device 116 within the end cap 110 in accordance with any suitable technique that would be evident to a person skilled in the art.

Figure 9:
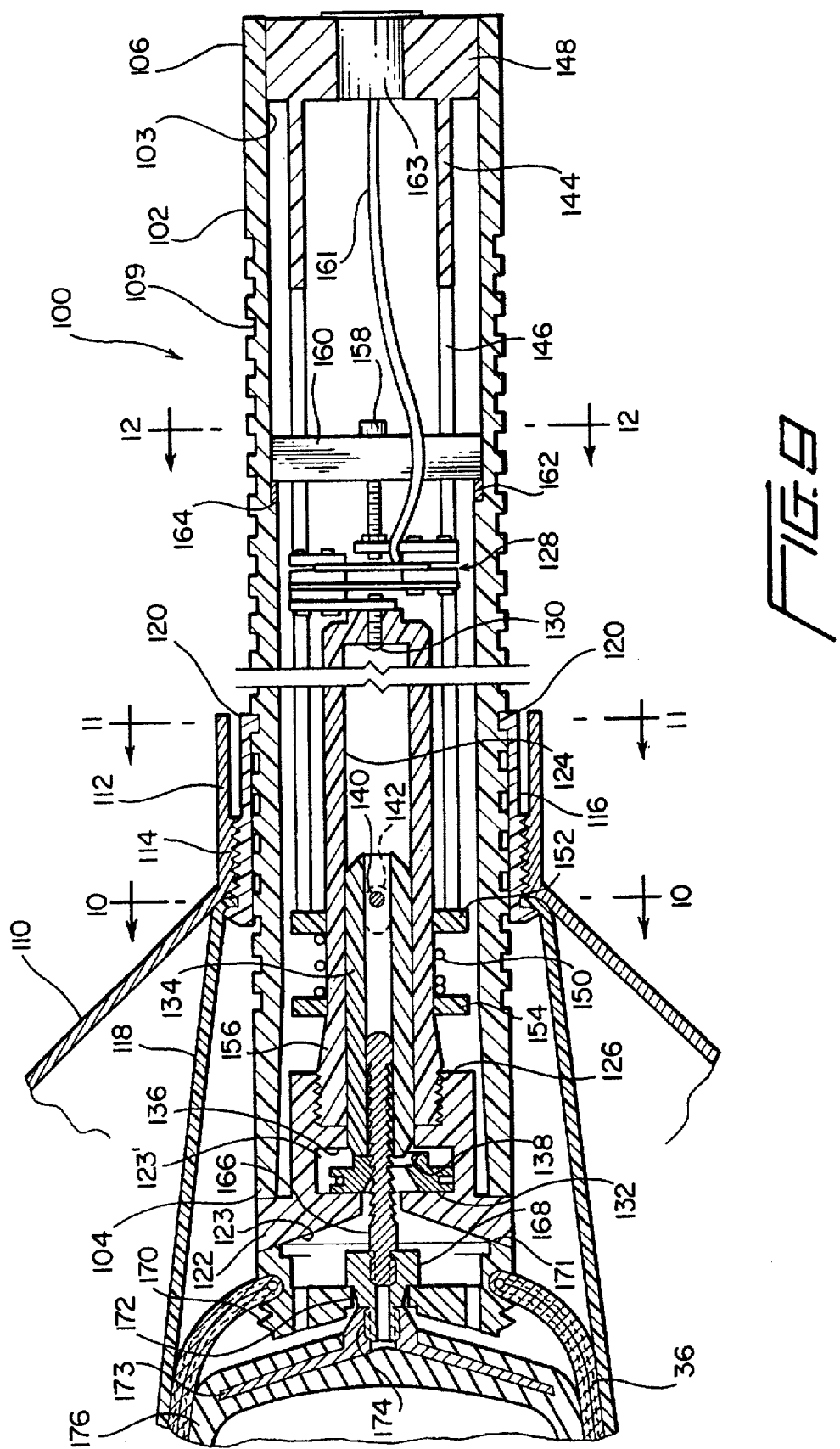
FIG. 9 is a side-elevation section view of an alternative embodiment of a tension connector system usable with the pressurized casting device of the invention.

Tension connector locking device 116 includes locking teeth 120 projecting radially inwardly as shown in FIGS. 9 and 11 for selective engagement with the detent grooves 109 in tubular member 102. The tension connector locking device 116 essentially comprises a thin annular flexible tube having discontinuous side wall portions resiliently biasing and supporting the teeth 120 whereby the teeth 120 can be sprung or deflected radially outwardly from a normal locking position against the bias of the material forming the tension connector locking device. For example, the tension connector locking device could be made of a molded synthetic resin such as nylon which would provide inherent resiliency for accommodating outward springing movement of teeth 120 in a manner to be described below.

From viewing FIGS. 9 and 11, it will be evident that rotation of tubular member 102 about its longitudinal axis will cause teeth 120 that are in locking engagement with grooves 109 to be deflected radially outwardly when the smooth outer surface portions 108 of the member 102 are moved under the teeth to cause the teeth to be cammed outwardly from the grooves 109. When the teeth engage the smooth outer surface 108, the tubular member 102 is free to move longitudinally within the tension connector locking device without engagement or locking of the teeth 120 with any grooves 109 so long as member 102 is not rotated. Slight rotation of the tubular member 102 to align the grooves 109 with teeth 120, however, will permit teeth 120 to snap radially inwardly into the closest available grooves 109 on the exterior of tubular member 102 to thereby lock the tubular member 102 against further longitudinal movement relative to the tension connector locking device 116 and the end cap 110 of the pressure casting device. Since the grooves 109 are closely spaced together, fine incremental adjustment of the position of tubular member 102 relative to the end cap 110 is enabled simply upon manipulation of the tubular member 102 in a rotational and longitudinal sense. The flat bottom configuration of the grooves tends to prevent inadvertent rotation of the tubular member 102 when locked.

The length of the tubular member 102 is selected such that it can be moved within the casting device end cap 110 in a longitudinal sense towards and away from a residual limb within the casting device and an end fitting associated with a silicone sleeve within the casting device, as will be explained more fully below. In this embodiment, the length of the tubular housing 102 is selected such that it may be moved within the end cap 110 to engage a tension pin associated with a shortest residual limb expected to be fitted with a molded socket while leaving sufficient length outside the end cap 110 to permit manipulation of the tubular member.

The tension connector 100 also includes a proximal end fitting 122 fitted to the proximal end 104 of tubular member 102, the end fitting including a concave, conical end surface 123 and a central cavity 123'. A longitudinally extending central bore extends through the end fitting 122, as shown in FIG. 9. End fitting 122 is secured by threads 126 to cylindrical force rod 124 that extends longitudinally within tubular member 102 from the proximal end area of the tubular member 102 towards the distal end thereof. The force rod 124 is connected at its distal end by fastener 130 to a load cell 128 by fastener 130. The load cell 128 may be the same type of mechanism is described previously in connection with load cell 84 illustrated in FIG. 4 or any other suitable load cell that will function in an equivalent manner.

A gripper mechanism 132 is provided in the central cavity of end fitting 122 and is retained therein by a suitable biasing means (not illustrated) normally maintaining the gripper 132 displaced to one side of the longitudinal axis of the end fitting 122. The gripper 132 includes internal teeth or detents arranged to engage external teeth or detents provided on a tension pin 166 such that the gripper permits longitudinal movement of the tension pin 166 towards the distal end of the tubular member 102 but prevents return movement of the pin until the gripper is released. This arrangement of gripper and tension pin corresponds with the arrangement described previously in connection with the embodiment of the invention illustrated in FIG. 2.

A gripper release device 134 comprises a tubular member having a conical nose end 136 arranged to engage a conical surface 138 of gripper 132. Conical nose end 136 of release 134 can be moved axially towards and away from the gripper 132 such that, when the nose end 136 is advanced towards the gripper 132, it acts as a cam surface and the conical surface 138 of gripper 132 acts as a follower surface so that the gripper 132 is displaced transversely or radially with respect to the longitudinal axis of the end fitting 122 when the release 134 is advanced towards the gripper 132. Essentially, the conical nose end 136 of release 134 causes centering of the gripper 132, thereby releasing its teeth from the teeth of the tension pin 166.

The gripper release 134 is supported in sliding relationship within the inner bore of the cylindrical force rod 124, as illustrated in FIG. 9. The gripper release 134, however, is secured by means of pin 140 extending through a longitudinal slot 142 in force rod 124 to a gripper release actuator rod 144 that extends longitudinally within the inner bore of tubular member 102 (see FIG. 10). The rod 144 includes an elongate slot 146 extending through the proximal end of the rod 144, while the remainder of the exterior surface of the rod 144 is cylindrical in contour as shown in FIG. 12. An enlarged head 148 is provided on the rod 144 to provide a close fit within the bore 103 of tubular member 102 and to act as a bearing surface between the head 148 and the bore 103.

A compression spring 150 on force rod 124 is retained by retainer discs 152, 154 and located at the proximal end of the actuator rod 144 for maintaining the rod 144 located such that the enlarged head 148 of the rod is located at the distal end 106 of tubular member 102. The compression spring 150 tends to spread the discs 152 and 154 apart, but the disc 154 is locked against longitudinal movement by an enlarged stop 156 provided on cylindrical force rod 124. Thus, spring 150 urges disc 152 and the proximal end of rod 144 towards the distal end of tubular member 102. The rod 144, on the other hand, is displaceable against the force of the compression spring 150 by moving the enlarged head 148 inwardly along the length of tubular member 102 so as to drive pin 140 and gripper release 134 longitudinally towards the gripper 132 to thereby selectively effect release of the gripper 132 in the manner described above. Upon return of the enlarged head 148 by, the spring 150, rod 144 is urged towards the distal end of tubular member 102 and withdraws the gripper release from the gripper 132 to enable the gripper to return to its normal position eccentric of the longitudinal axis of end fitting 122. It will be noted that the spring 150 tends to hold the discs 152, 154 apart longitudinally within tubular member 102 to thereby drive the rod 144 back towards its normal position at the distal end 106 of tubular member 102. Thus, release of gripper 132 can be accomplished remotely by manually pressing the enlarged head 148 effectively as a push-button.

The load cell 128 is rigidly connected to the distal end of force rod 124 by a suitable fastener 130, as previously described. The load cell 128 is also connected to a load transmitting member 160 through an adjustable fastener or the like 158. The load transmitting member 160 is located within an enlarged portion of the inner bore 103 of tubular member 102 and engages a suitable metallic ring 162 or the equivalent retained in shoulder 164 of tubular member 102 at the end of the enlarged section of the bore 103 (FIGS. 9 and 12). Thus, load transmitting member 160 is prevented from axial movement within the bore 103 beyond the ring 162 in the direction of the proximal end of tubular member 102.

It will thus be seen that tension load generated during the casting process as previously described and transmitted through end cap 110 to the tension connector lock 116 and its teeth 120 is in turn transmitted through tubular member 102 to cause load transmitting member 160 to move with the tubular member 102 and end cap 110 in a distal direction during casting.

The load transmitted through load transmitting member 160 is transmitting to the load cell 128 through the adjustable fastener 158 and this load is reacted by the force rod 124 in tension. This tension force transmitted through force rod 124 in turn is transmitted to the gripper 132 through the end fitting 122 which engages the tension pin 166, as previously described. Thus, axial loading between the end cap 110 and the residual limb within the casting device is transmitted through the load cell 128 which, as previously described, is electrically actuated so as to produce an electrical output signal indicative of the load. An appropriate lead or leads 161 connected to an electrical connector 163 located in the enlarged end 148 of gripper release rod 144 enables energization of the load cell 128 and the availability of output signals indicative of the load sensed by the load cell at the connector 163.

Further in accordance with this embodiment of the invention, tension pin 166 is provided with a threaded head end 168 that extends through prosthesis coupler 170 via a central bore 172. The threads of the head end 168 of pin 166 are received by the threaded socket 174 provided in the end fitting 173 of silicon sleeve 176 that is in direct engagement with a residual limb to be fitted with a prosthetic socket in accordance with the invention. The head 168 of pin 166 effectively clamps the prosthesis coupler 170 to the silicone sleeve 176 and its end fitting 173 so that tension loads applied through pin 166 will be transmitted to the silicone sleeve 176 as well as the terminal end of the pre-form 36 during hardening of the pre-form while it is under compression through the pressure membrane 118.

It will be noted that the concave conical end surface 123 of end fitting 122 enables the pin 166 to be located in the center of the end fitting to enable the pin to extend through gripper 132 when tension connector 100 is moved in the direction of the proximal end of the casting device.

In operation, the embodiment of the invention in accordance with FIGS. 9–12 operates in essentially the same manner as the embodiment described in FIGS. 2–5. After the silicone sleeve 41 or 176 has been donned over the residual limb 40, the pre-form 36 with its associated prosthesis coupler 38 or 170 is rolled up over the silicone sleeve and pressed into close engagement with the sleeve and its contained residual limb. The tension pin 44 or 166 is threaded into the end fitting 42 or 173 so that it extends in a distal direction within pressure membrane 22 or 118.

The assembled tension connector 58 or 100 is then advanced longitudinally through the end cap 16 or 110 such that the tension pin extends through the gripper associated with the tension connector of all embodiments. In accordance with the embodiment of FIGS. 9–12, a slight pre-tension may be applied to the tension pin 166 by pulling on the tension connector after the pin 166 has been engaged by the gripper 132. The tension connector 100 is then rotated sufficiently to lock the cylindrical member 102 into engagement with the teeth 120 to thereby secure the tension connector 100 against longitudinal movement relative to end cap 110.

In all embodiments, application of a pressurized fluid into the pressurizing space 20 (FIG. 4) causes external pressurization of the pre-form 36 in the manner described previously and a resultant reaction load to be applied in a distal direction to the tension pin 132. Hardening of the pre-form 136 then proceeds to completion, following which the tension pin is released from its gripper and the residual limb with the molded and hardened socket are removed from the proximal end of the casting device. The molded socket is removed from the residual limb and final cutting, shaping (trumpeting) and finishing operations are performed thereon in accordance with known techniques.

It is to be understood that preferred or best mode embodiments of the invention have been described for illustrative purposes only and that the scope of the invention is to be limited only by the scope of the claims that follow.

We claim:

1. Apparatus for forming a definitive prosthesis socket for a residual limb that includes soft tissue and a distal end area, comprising:

tension applying means for applying tension to the distal end area of a residual limb so as to effectively elongate the soft tissue of such residual limb and cause its diametrical reduction;

a moldable definitive socket forming material configured to enclose a distal end area of a residual limb, said forming material being hardenable when subject to an activating agent to a hardened state in which the forming material possesses load bearing structural properties enabling the forming material to function as a definitive prosthesis socket;

retaining means for retaining the socket forming material at a casting location;

compression means for circumferentially compressing the socket forming material at said casting location, and means for activating said compression means;

means for activating said tension applying means while said casting material is located at said casting location and while said compression means is activated;

said retaining and tension applying means comprising said compression means and a tension transfer element connecting the residual limb distal end area to the compression means, said compression applying means being supported by the distal end area of the residual limb at said casting location and arranged to be displaced away from the residual limb distal end area during circumferential compression of the residual limb distal end area, said compression means being substantially unrestrained against motion in a direction away from the residual limb distal end area during said circumferential compression except by said tension transfer element, to thereby effect transfer of compression means displacement motion away from the residual distal end area during circumferential compression of the socket forming material to tension force in the residual limb distal end area during activation of the compression means.

2. Apparatus as claimed in claim 1, wherein said tension applying means comprises a suction elastomeric residual limb sleeve having a distal end and said tension transfer element comprises means for distally tensioning the sleeve distal end.

3. Apparatus as claimed in claim 1, wherein said tension applying means is arranged to tension a residual limb distal end area locatable within said moldable definitive socket material after said socket material has been arranged so as to envelop such residual limb distal area.

* * * * *